US00PP25020P3

(12) United States Plant Patent
Korlipara

(10) Patent No.: US PP25,020 P3
(45) Date of Patent: Oct. 28, 2014

(54) ***PLECTRANTHUS* PLANT NAMED 'VELVET ELVIS'**

(50) Latin Name: ***Plectranthus* hybrid**
Varietal Denomination: Velvet Elvis

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 176 days.

(21) Appl. No.: 13/694,685

(22) Filed: Dec. 20, 2012

(65) Prior Publication Data

US 2014/0182037 P1 Jun. 26, 2014

(51) Int. Cl.
*A01H 5/00* (2006.01)

(52) U.S. Cl.
USPC ..... Plt./469

(58) Field of Classification Search
USPC ..... Plt./469
See application file for complete search history.

*Primary Examiner* — Annette Para
(74) *Attorney, Agent, or Firm* — Klarquist Sparkman, LLP

(57) ABSTRACT

A new and distinct form of *Plectranthus* plant characterized by long inflorescences with large lavender flowers, an upright, shrubby habit, a long bloom time, very dark green leaves with dark backs, and excellent vigor.

1 Drawing Sheet

Botanical denomination: *Plectranthus* hybrid.
Variety designation: 'Velvet Elvis'.

BACKGROUND OF THE INVENTION

The present invention relates to a new and distinct cultivar of *Plectranthus*, given the name, 'Velvet Elvis'. *Plectranthus* is in the family Lamiaceae. This plant originated from a planned breeding program for an improved *Plectranthus* hybrid. The parents were proprietary, unreleased seedlings.

Compared to *Plectranthus* Mona Lavender, patented as 'Plepalila', U.S. Plant Pat. No. 13,858, the new cultivar has much larger flowers and inflorescences, and deeper green foliage.

*Plectranthus* 'Velvet Elvis' is uniquely distinguished by:

1. long inflorescences with large lavender flowers,
2. upright, shrubby habit,
3. long bloom time,
4. very dark green leaves with dark backs, and
5. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a one-year-old *Plectranthus* 'Velvet Elvis' growing in a five-gallon container in a warm greenhouse in May in Canby, Oreg.

DETAILED PLANT DESCRIPTION

The following is a detailed description of the new *Plectranthus* cultivar based on observations in May of one-year-old specimens grown in a warm greenhouse in Canby, Oreg. The color descriptions are all based on *The Royal Horticultural Society Colour Chart,* 5$^{th}$ edition.

Plant:

*Type*.—Perennial.
*Form*.—Shrubby.
*Cold hardiness*.—USDA Zone 10.
*Size*.—Grows to 78 cm wide and 74 cm high.
*Vigor*.—Excellent.

Stem:

*Size*.—Grows to 65 cm long and 2 cm wide.
*Internodes*.—2 cm to 8 cm long.
*Surface texture*.—Young stems pubescent.
*Shape in cross section*.—Square.
*Color*.—Young stems, Green N137A; old stems, closest to Brown N199B.
*Rooting*.—Plants root easily from stem cuttings.

Leaf:

*Type*.—Simple, semi-succulent.
*Arrangement*.—Opposite.
*Shape*.—Ovate to broadly ovate.
*Venation*.—Pinnate.
*Margins*.—Coarsely serrate.
*Apex*.—Acute.
*Base*.—Cuneate.
*Blade size*.—Grows to 8.5 cm long and 7 cm wide.
*Surface texture*.—Pubescent on both sides.
*Petiole*.—Grows to 5 cm long and 2 mm wide, pubescent, topside Green N137A, bottom side Greyed Purple N186B.
*Leaf color*.—Topside, closest to Green 139A, but much darker with veins 139A; bottom side Greyed Purple N186B with veins N186B.

Inflorescence:

*Type*.—Terminal raceme with flowers solitary in short pedicelled, 3-flowered verticils positioned at right angles to the stem.
*Number of flowers*.—About 50.

*Size of inflorescence*.—Grows to 24 cm long and 7.5 cm wide.

*Pedicel*.—5 mm long and 1 mm wide, pubescent, Greyed Purple N186A.

*Bloom period*.—Year round in the greenhouse in Canby, Oreg.

Flower bud:

*Size*.—25 mm long and 5 mm wide at the widest point prior to opening.

*Description*.—Tubular, dorsally flattened.

*Surface texture*.—Pubescent.

*Color*.—Violet 86B on the top of the tube with White NN155D on the bottom edge and base of the tube; Violet 86A on the end where the lobes will be.

Flower:

*Type*.—Zygomorphic.

*Shape*.—Bilabiate, tubular.

*Size*.—35 mm long and 24 mm wide.

*Corolla description*.—Grows to 35 mm long and 24 mm wide; glabrous inside and out; tube 24 mm long and 5 mm wide, Violet N88C outside and Violet 85C inside; upper lip 4 lobed, back sides Violet 86C, front sides Violet 85C with spots N88A, 2 top lobes joined to form one flare 13 mm long and 18 mm wide, each lobe ovate, tip obtuse, margin entire, 2 lateral lobes each 1.5 mm deep and 7 mm wide, tip obtuse, margin entire; lower lobe boat-shaped, 12 mm long and 5 mm wide, 2 lobed, margin entire, tip obtuse, Violet 85A on back and Violet 85C with spots N88A on inside.

*Calyx description*.—Bilabiate with broad upper lip and lower lip comprised of four pointed lobes fused at base, 3 mm long and 3 mm wide, Greyed Purple N186A, pubescent outside and glabrous inside, broad upper lip 2 mm wide and 1.5 mm long, broadly ovate with an acute tip, margins entire; lower lip lobes lanceolate, 2 mm long and less than 1 mm wide, tips acuminate, margins entire.

*Pistil description*.—1, 33 mm long, ovary 0.5 mm long, Yellow Green 146C, style 32 mm long, Violet 85C to 85D, stigma two-parted, 0.5 mm, 85D.

*Stamen description*.—4 in number, paired and exerted, top two 34 mm long with the bottom 21 mm fused to the corolla tube and bottom two 32 mm long with the bottom 21 mm fused to the corolla tube, filaments White NN155C, anthers 0.5 mm long, Violet Blue 96D, pollen White NN155C.

*Fragrance*.—None.

*Lastingness*.—A flower last about a week.

Fruit/seed: None seen.

Pests and diseases: Resistance to diseases common to *Plectranthus* has not been observed. The new cultivar has shown no problems in Canby, Oreg.

I claim:

1. A new and distinct form of *Plectranthus* plant substantially as shown and described.

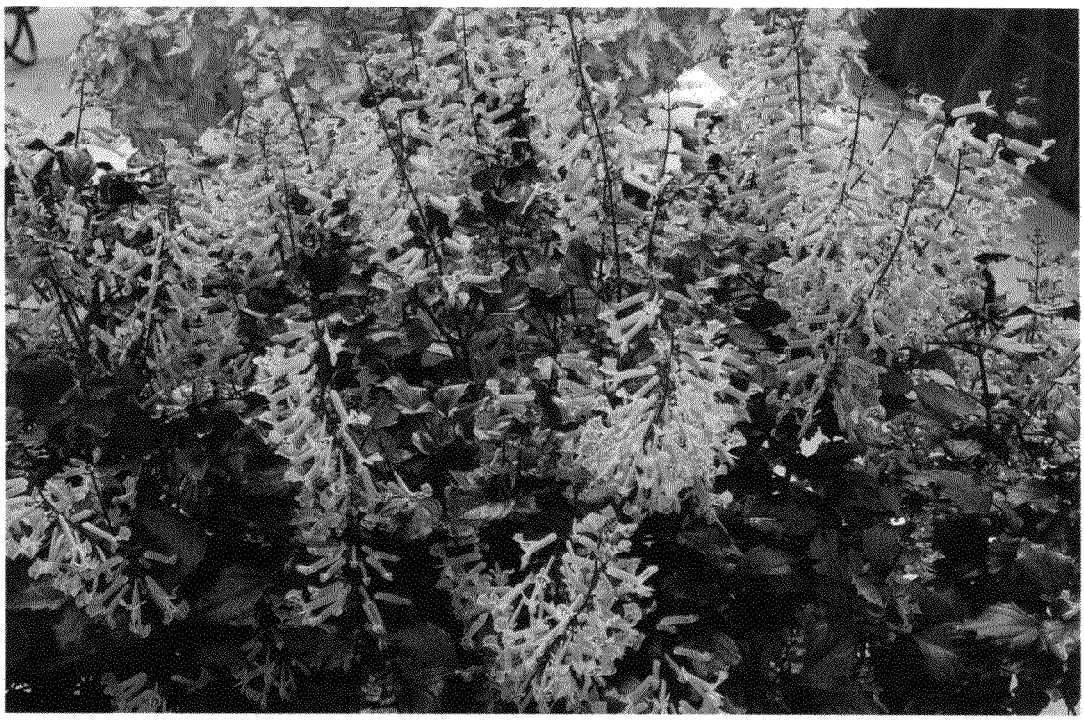

* * * * *